United States Patent
Willner et al.

(10) Patent No.: US 11,644,457 B2
(45) Date of Patent: May 9, 2023

(54) DEVICE, SUBSTANCE MEASURING DEVICE, PROCESS, COMPUTER PROGRAM, CAMERA AND CELL PHONE FOR THE IDENTIFICATION OF A SUBSTANCE MEASURING DEVICE

(71) Applicant: Dräger Safety AG & Co. KGaA, Lübeck (DE)

(72) Inventors: Matthias Willner, Lübeck (DE); Alexander Sarcinelli, Ahrensburg (DE); Stefan Morley, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 53 days.

(21) Appl. No.: 16/325,322

(22) PCT Filed: Aug. 9, 2017

(86) PCT No.: PCT/EP2017/000966
§ 371 (c)(1),
(2) Date: Feb. 13, 2019

(87) PCT Pub. No.: WO2018/033240
PCT Pub. Date: Feb. 22, 2018

(65) Prior Publication Data
US 2019/0178869 A1   Jun. 13, 2019

(30) Foreign Application Priority Data

Aug. 15, 2016   (DE) .................... 10 2016 009 834.1

(51) Int. Cl.
*G01N 33/497*   (2006.01)
*A61B 5/00*   (2006.01)
*G16H 40/63*   (2018.01)
*G16H 40/67*   (2018.01)
*G01N 33/98*   (2006.01)

(52) U.S. Cl.
CPC ....... *G01N 33/4972* (2013.01); *A61B 5/4845* (2013.01); *G01N 33/98* (2013.01); *G16H 40/63* (2018.01); *G16H 40/67* (2018.01)

(58) Field of Classification Search
CPC .... G01N 33/4972; G01N 33/98; G16H 40/67; G16H 40/63; A61B 5/4845
USPC ..................................................... 235/462.1
See application file for complete search history.

(56) References Cited

U.S. PATENT DOCUMENTS

| 6,748,792 | B1 | 6/2004 | Freund et al. | |
| 8,006,911 | B2 * | 8/2011 | Yi | G06K 1/123 235/494 |
| 2007/0145137 | A1 * | 6/2007 | Mrowiec | A61B 5/00 235/375 |

(Continued)

FOREIGN PATENT DOCUMENTS

| EP | 2 075 151 A1 | 7/2009 |
| EP | 2 127 599 A1 | 12/2009 |

(Continued)

*Primary Examiner* — Michael G Lee
*Assistant Examiner* — David Tardif
(74) *Attorney, Agent, or Firm* — McGlew and Tuttle, P.C.

(57) ABSTRACT

A device (10), a substance measuring device (100), a process, a computer program, a camera (200) and a cell phone are provided for the unique and individual identification of a substance measuring device (100) of a test subject (300). The device (10) includes an optical identifier (12).

13 Claims, 4 Drawing Sheets

(56) References Cited

U.S. PATENT DOCUMENTS

| | | | |
|---|---|---|---|
| 2008/0170762 A1 | 7/2008 | Endo et al. | |
| 2009/0008453 A1* | 1/2009 | Ikeda | B42D 25/309 |
| 2011/0186632 A1* | 8/2011 | Yi | G06K 7/1093 |
| | | | 235/462.04 |
| 2012/0109688 A1* | 5/2012 | Yoo | G16H 40/67 |
| | | | 705/3 |
| 2013/0066562 A1* | 3/2013 | Hengstler | G16H 40/40 |
| | | | 702/19 |
| 2014/0041436 A1 | 2/2014 | Knott et al. | |
| 2014/0064619 A1* | 3/2014 | Decoux | G06K 19/06037 |
| | | | 235/494 |
| 2015/0204844 A1* | 7/2015 | Nothacker | G01N 33/4972 |
| | | | 73/23.3 |
| 2015/0360696 A1 | 12/2015 | Yi et al. | |
| 2016/0050309 A1 | 2/2016 | Gooberman | |
| 2019/0178869 A1* | 6/2019 | Morley | G16H 40/67 |

FOREIGN PATENT DOCUMENTS

| | | |
|---|---|---|
| EP | 2 237 034 A1 | 10/2010 |
| WO | 2012/041505 A1 | 4/2012 |
| WO | 2017/064023 A1 | 4/2017 |

\* cited by examiner

DEVICE, SUBSTANCE MEASURING DEVICE, PROCESS, COMPUTER PROGRAM, CAMERA AND CELL PHONE FOR THE IDENTIFICATION OF A SUBSTANCE MEASURING DEVICE

CROSS REFERENCE TO RELATED APPLICATIONS

This application is a United States National Phase Application of International Application PCT/EP2017/000966 filed Aug. 9, 2017, and claims the benefit of priority under 35 U.S.C. § 119 of German Application 10 2016 009 834.1, filed Aug. 15, 2016, the entire contents of which are incorporated herein by reference.

TECHNICAL FIELD

The present invention pertains to a device, to a substance measuring device, to a process, to a computer program, to a camera and to a cell phone for the identification of a substance measuring device, especially but not exclusively, to an optical identifier for the identification of the substance measuring device.

TECHNICAL BACKGROUND

Various concepts which make it possible to monitor a patient outside of facilities specially provided for this, for example, in case of alcohol addiction and/or drug addiction, are known in conventional technology. Home visits can be carried out by means of mobile staff, or the patients can be monitored on an outpatient basis by routinely coming in and providing samples. This leads to a corresponding effort for the patient or for the health care staff. The example of alcohol addiction will be taken into consideration below as representative for alcohol addiction, drug addiction or addiction, in general, and monitoring strategies connected therewith for the respective substances.

E.g., the measurement of the alcohol content in the breathing air is described by the determination of breath alcohol. In the case of drug monitoring, saliva samples can be used as a suitable means for monitoring consumption and/or abstinence of a patient. For example, a gas exchange between the breathing air and the absorbed alcohol takes place in the pulmonary alveoli after consumption of alcohol-containing beverages or foods. The alcohol contained in the peripheral blood is absorbed by the fresh air inhaled and discharged with the exhaled air, as a result of which a measurement can be carried out, which makes it possible to infer the blood alcohol concentration.

Hand-held devices (mobile devices) as well as stationary devices can be used for the determination of breath alcohol. The breath alcohol value is determined by a measurement in an electrochemical or physical manner and is shown on a display unit (usually display screens/displays).

The principal field of application of breath alcohol determination are traffic stops in road traffic by the police. However, so-called "alcohol testers" are also used for personal use, in the medical field (detox centers) or in the applications "alcohol ignition interlock device" and "home monitoring." In the latter, the so-called "offender programs," a photo is frequently required by law when providing a sample in order to ensure that the person providing the sample and the offender are the same person.

For example, there is a concept, which provides for a solution via a combination of a breath alcohol measuring device and a smartphone (cell phone), including a corresponding application (app) for the smartphone in the area of home monitoring. A photo can be taken with a camera integrated in the alcohol measuring device during the providing of a sample in some solutions.

SUMMARY

Therefore, there is a need to provide an improved concept for monitoring a patient.

Exemplary embodiments are based on the finding that reliable information on whether the person providing the sample and the offender are the same person during a required breath test/substance test is helpful in the area of home monitoring. A home monitoring program may be, for example, a condition of probation for repeat offenders of alcohol/drug abuse in road traffic or in the family household with possible domestic violence. E.g., a condition of probation may require randomized breath alcohol tests or saliva sample tests during the day. A verification function via photo may be implemented in some exemplary embodiments, so that it is transparent whether the person who is providing the sample is also the repeat offender.

Some exemplary embodiments provide for a combination of a substance measuring device and a smartphone. An app is installed on the smartphone, with which the person providing the sample can carry out the following steps, 1. The smartphone is started, the breath alcohol device also starts automatically;
2. The person (user) providing the sample starts the app via a button on the smartphone;
3. A user interface prompts the test subject (user) to align the smartphone such that the face of the test subject can be photographed by the front camera of the smartphone during the providing of the sample;
4. An acknowledgment appears that the smartphone is positioned correctly;
5. The user is prompted to provide a breath alcohol test;
6. The user actuates a button in order to start the test;
7. The user blows into the device while the user continues to position the smartphone in the same way;
8. A photo is taken during the providing of the sample;
9. The person providing a sample knows when the test is completed by means of an indicator; and
10. Test results and photo are stored on the smartphone and sent to a legally authorized person.

In such exemplary embodiments, it can be proven via a manual examination of the available photos that the person providing the sample is actually the person who has provided the breath alcohol test. This checking via manual examination alone can be extensive and time-consuming. The possibility of determining violations by means of random samples can be rather low. Such violations as, for example, the situation where the person providing the sample takes a photo of himself, but lets a different person do the blowing for him, cannot always be avoided. In addition, there is a kind of manipulation, in which the offender purchases a new device and subsequently lets a third person provide the sample and he himself only simulates taking the test with the recently purchased device and thus appears undeniably in the photo with the device. Exemplary embodiments are therefore further based on the idea to make the substance measuring device identifiable.

Therefore, exemplary embodiments provide a device for the unique and individual identification of a substance measuring device of a test subject, wherein the device comprises an optical identifier. An optical identifier can make it possible to identify the substance measuring device. In addition, exemplary embodiments provide a substance measuring device with such a device.

In exemplary embodiments, a substance measuring device may be associated or may already have been associated with a person, for example, within the framework of a monitoring or a home monitoring. The terms "remote monitoring" (in the sense of general remote monitoring) or "home alcohol monitoring" may also be used in this connection. The optical identifier can then be used to verify that the substance measuring device and the person providing the sample are associated with one another or linked with one another. At least some exemplary embodiments can thus make it possible to check this association or connection/link and determine information on whether the person providing the sample during the providing of the sample is also the correct person, who is using the substance measuring device that is individually associated with the person providing the sample. Exemplary embodiments can thus make it possible to verify an association between a substance measuring device and a test subject. The device can be configured for the verification or checking of an association between the substance measuring device and the test subject. At least some exemplary embodiments can achieve an improved success rate in the monitoring due to the link between person/test subject and substance measuring device than this would be the case, for example, in case of a link between the substance measuring device and a location or a vehicle.

The optical identifier can accordingly be provided on or in the substance measuring device in order to make it possible to at least temporarily recognize the substance measuring device and thus to check the association between the substance measuring device and the person providing the sample, as the exemplary embodiments explained in detail below will show. The optical identifier here may be permanent, for example, as an external feature, or even temporary, for example, an optical signal can be used via a light source or a display. In some exemplary embodiments, the optical identifier may also be unique and one of a kind, if the substance measuring device can be distinguished from all other substance measuring devices. In general, the term, "unique and individual" identification here is not theoretical, however, but rather is defined as practical and in this case means that the substance measuring device can be recognized by the optical identifier with a certain probability of, e.g., >90%, 95%, 99%, 99.9%, 99.99%, etc. as the substance measuring device associated with the person providing the sample. In other words, "unique and individual" identification may also be interpreted to the effect that a substance measuring device associated with a person providing the sample can be recognized by means of the optical identifier with a probability of error of less than 10%, 1%, 0.1%, 0.01%, 0.001%, etc. In exemplary embodiments, the recognition can take place by means of optical image detection (photo, video) and digital image processing.

In this connection, a substance to be measured may correspond to a breath alcohol and/or narcotics in the saliva of the test subject. In some other exemplary embodiments, the optical identifier may comprise a geometric configuration of one or more markers, a barcode, and/or a quick response (QR) code for a housing of the substance measuring device. The markers or optical codes may be helpful in the identification of the substance measuring device. The geometric configuration may correspond to a configuration within a triangle. A triangular configuration may offer advantages in case of recognition from different angles of view because a triangle is relatively robust in its shape in this regard. Thus, in some exemplary embodiments, the geometric configuration may comprise at least three markers, which are arranged along the sides of a triangle.

In some other exemplary embodiments, the optical identifier may comprise one or more reflectors. Reflectors can offer advantages, especially in case of electronic or digital detection. The optical identifier can in other exemplary embodiments comprise one or more reflective foil sections. Foil sections offer the advantage that they can be applied or can be mounted in a simple manner on a housing of a substance measuring device.

In some exemplary embodiments, the optical identifier may comprise a unique identifier. The substance measuring device can thus be uniquely identified by means of the optical identifier. The optical identifier may comprise a sequence of optical signals that can be generated by one or more light sources arranged on the substance measuring device. The optical identifier can thus also be variable in some exemplary embodiments or cannot be directly recognized from the outside. The light sources can be configured to emit light in an invisible range (a frequency range of light not visible to humans). Thus, the identifier cannot be recognized without additional aids. The light sources can further be configured to emit light in an infrared range. Exemplary embodiments can thus be implemented in a simple manner, and housings that are nontransparent in the visible light range, through which it is possible to shine through by means of infrared light, may be used as well. The one or more light sources can thus be protected by the housing.

Exemplary embodiments also provide a process for the unique and individual identification of a substance measuring device of a test subject, wherein the substance measuring device has an optical identifier. The process comprises the carrying out of a substance measurement by the test subject and the detection of optical image data of the test subject together with the substance measuring device during the substance measurement. The process further comprises the determination of information on whether the optical identifier can be detected in the image data and the identification of the substance measuring device based on the optical identifier. In some exemplary embodiments, the process can further comprise the passing on of the image data together with the information on the checking.

Exemplary embodiments further provide a camera, which is configured to carry out a process being described here. In some other exemplary embodiments, the camera may further comprise a memory and may be configured to store the image data together with the information. A further exemplary embodiment is a cell phone with the camera according to the above description. The cell phone can in some exemplary embodiments be configured in its function for the identification of the substance measuring device with the camera and can be limited in its other functions. The cell phone can be configured to be able to make calls to no more than three predefined telephone numbers in some other exemplary embodiments.

A further exemplary embodiment is a computer program for executing at least one of the processes described above, when the computer program is running on a computer, on a processor or on a programmable hardware component. A further exemplary embodiment is also a digital storage medium, which is machine- or computer-readable, and which has electronically readable control signals which can interact with a programmable hardware component such that one of the processes described above is executed.

Further advantageous configurations are described in detail below on the basis of the exemplary embodiments shown in the drawings, to which, however, not all exemplary embodiments are, in general, limited. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
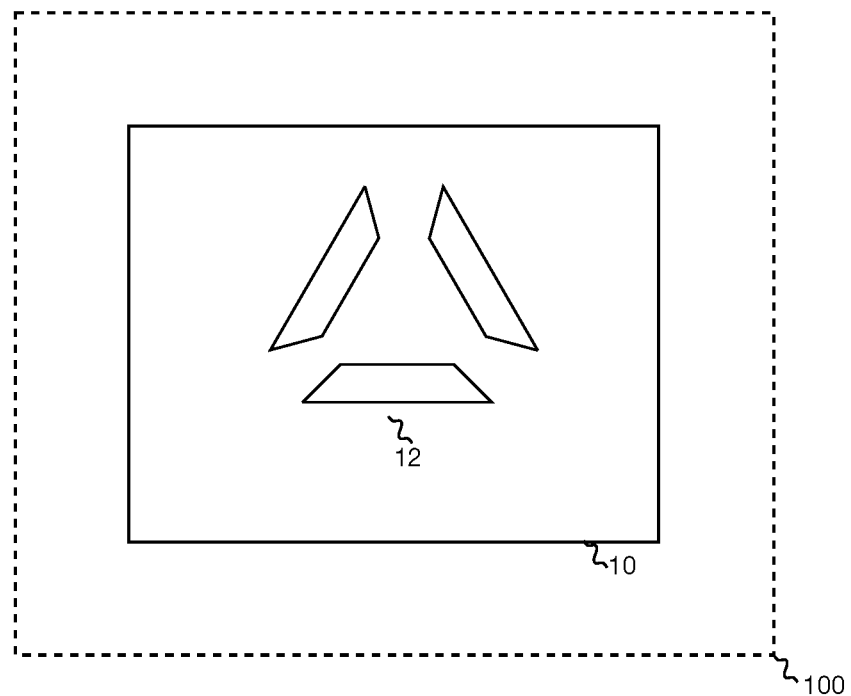
FIG. 1 is a schematic view showing an exemplary embodiment of a device for the identification of a substance measuring device.

Referring to the drawings, different exemplary embodiments will now be described in detail with reference to the attached drawings, in which some exemplary embodiments are shown.

In the following description of the attached figures, which show only some examples of exemplary embodiments, identical reference numbers may designate identical or comparable components. Further, summary reference numbers may be used for components and objects that are present as a plurality of components and objects in an exemplary embodiment or in a drawing, but are described jointly in respect to one or more features. Components or objects that are described with identical or summary reference numbers may have an identical configuration in respect to individual features, a plurality of features or all features, for example, their dimensions, but they may possibly also have different configurations unless something different appears explicitly or implicitly from the description. Optional components are represented by broken lines or arrows in the figures.

Even though exemplary embodiments may be modified and varied in different ways, exemplary embodiments are shown in the figures as examples and will be described in detail herein. It should, however, be made clear that exemplary embodiments are not intended to be limited to the respective disclosed forms, but exemplary embodiments shall rather cover all functional and/or structural modifications, equivalents and alternatives, which are within the scope of the present invention. Identical reference numbers designate identical or similar elements in the entire description of the figures.

It should be noted that an element that is described as being "connected" or "coupled" with another element may be connected or coupled directly with the other element or elements located between them may be present. If, by contrast, an element is described as being "connected directly" or "coupled directly" with another element, no elements located between them are present. Other terms, which are used to describe the relationship between elements, shall be interpreted in a similar manner (e.g., "between" versus "directly between," "adjoining" versus "directly adjoining," etc.).

The terminology that is used here is used only to describe certain exemplary embodiments and shall not limit the exemplary embodiments. As being used here, the singular forms "a," "an" and "the" shall also include the plural forms unless the context unambiguously indicates something different. It should further be made clear that such terms as, e.g., "contains," "containing," "has," "comprises," "comprising" and/or "having," as used here, indicate the presence of said features, integers, steps, work processes, elements and/or components, but they do not rule out the presence or the addition of a feature or of one or more features, integers, steps, work processes, elements, components and/or groups thereof.

Unless defined otherwise, all the terms being used here (including technical and scientific terms) have the same meaning that a person having ordinary skill in the art to which the exemplary embodiments belong attributes to them. It should further be made clear that terms, e.g., those that are defined in generally used dictionaries, are to be interpreted such as if they had the meaning that is consistent with their meaning in the context of the relevant technology, and they are not to be interpreted in an idealized or excessively formal sense, unless this is expressly defined here.

FIG. 1 shows an exemplary embodiment of a device 10 for the unique and individual identification of a substance measuring device 100 of a test subject, wherein the device 10 comprises an optical identifier 12. Exemplary embodiments also provide a substance measuring device 100, comprising a body (a housing), with the device 10. The substance to be measured corresponds in this case to a breath alcohol and/or narcotics in the saliva of the test subject. Accordingly, the substance measuring device 100 is, for example, a mobile breath alcohol measuring device or a measuring device for detection of drugs in saliva samples. The designation "mobile" indicates in this case that the device can be used, e.g., in case of home monitoring, wherein the device can be wired or can be operated only by battery or rechargeable battery.

Unique and individual identification here means that the substance measuring device 100 can be recognized via the optical identifier 12 and can be distinguished from other substance measuring devices. Thus, the optical identifier 12 can be unique in some exemplary embodiments in relation to the substance measuring device 100, so that there is only one substance measuring device 100 with this optical identifier 12. The optical identifier 12 thus makes the ability to manipulate difficult, especially by using other possibly identical substance measuring devices. In some exemplary embodiments, it can thus be verified that a certain substance measuring device 100 available to a test subject was also used for providing a sample. The device 10 is then configured for verification of an association between the substance measuring device 100 and the test subject 300. The optical identifier 12 is therefore configured to make the substance measuring device 100 recognizable in photo material (photo or video) and distinguishable from other substance measuring devices. In this case, different types of optical identifiers can be used, and permanent identifiers and/or even temporary identifiers or verification signals can be used, as will still be explained in detail below.

The optical identifier 12 is a geometric configuration of one or more markers in the exemplary embodiment shown in FIG. 1, there being three markers in FIG. 1. The geometric configuration corresponds to a configuration within a triangle. The geometric configuration comprises at least the three markers, which are arranged along the sides of a triangle. The three markers are configured as reflective foil in this exemplary embodiment. Accordingly, the optical identifier 12 comprises in this exemplary embodiment one or more reflectors and one or more reflective foil sections.

Figure 2:
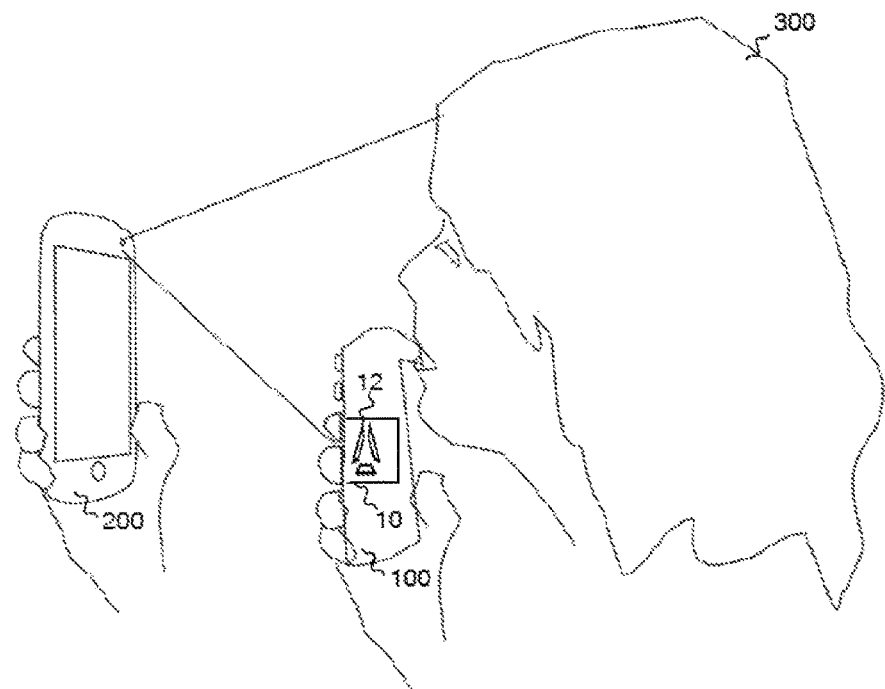
FIG. 2 is a schematic view showing a further exemplary embodiment of a device for the identification of a substance measuring device being used by a test subject.

FIG. 2 shows a further exemplary embodiment of a device 10 for the identification of a substance measuring device 100 being used by a test subject 300. FIG. 2 shows a mobile camera 200, which is integrated, for example, in a cell phone. The camera 200 is configured to photograph or take a video of the test subject 300 during a substance measurement with the substance measuring device 100 and thus to also record image data of the optical identifier 12 of the device 10 at the same time. For example, the optical identifier 12 can be recognized using digital image processing means, and it can thus be determined that the correct substance measuring device 100 was imaged into the image data.

Figure 3:
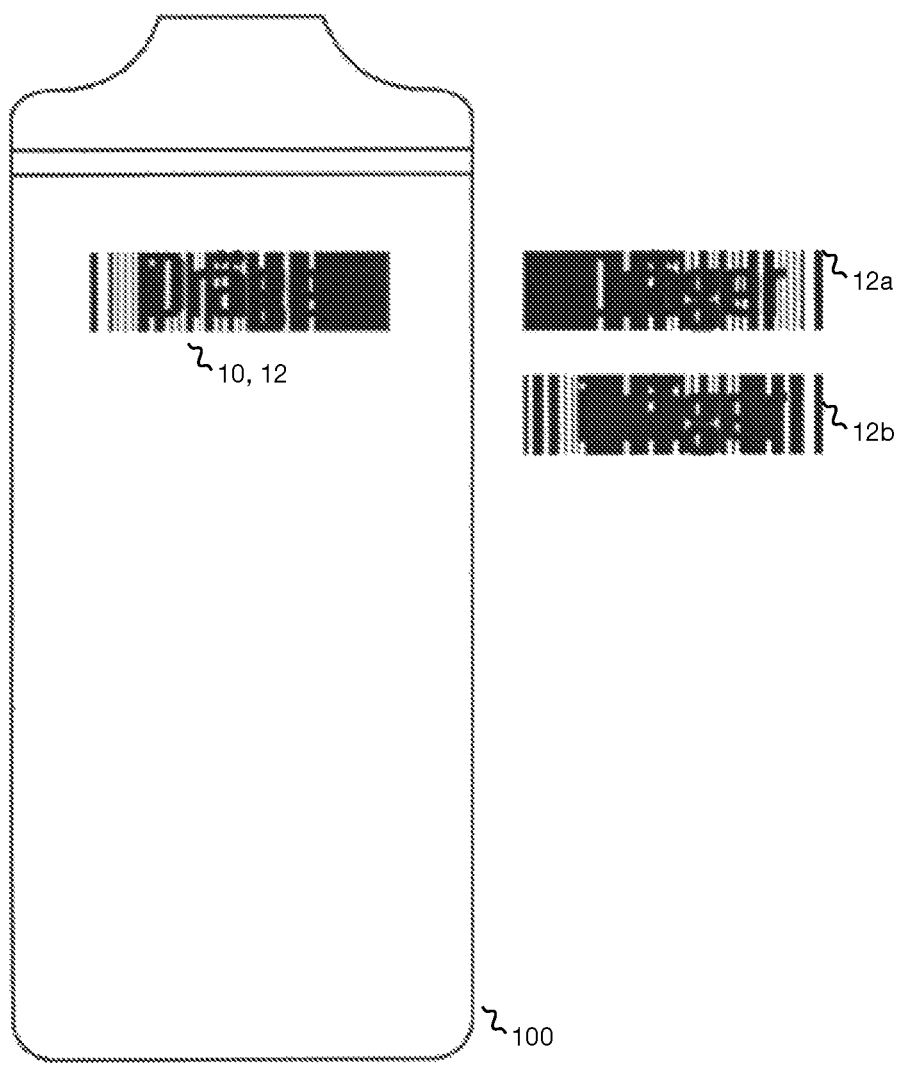
FIG. 3 is a schematic view showing exemplary embodiments of substance measuring devices with different identifiers.

In further exemplary embodiments, other optical identifiers may also be used, further examples are one or more barcodes and/or one or more QR codes on the housing of the substance measuring device 100. FIG. 3 shows exemplary embodiments of substance measuring devices 100 with different identifiers 12, 12a, 12b, which are configured as logos, here "Dräger," overprinted with barcodes. Optical codes (bar, QR, etc.) offer, for example, a large number of images and also the possibility of providing a unique identifier here. In some exemplary embodiments, the optical identifier 12 comprises a unique identifier. In addition to static optical codes such as barcodes and QR codes, a further example of a unique identifier is the use of a sequence of optical signals, as will still be explained in more detail below.

Figure 4:
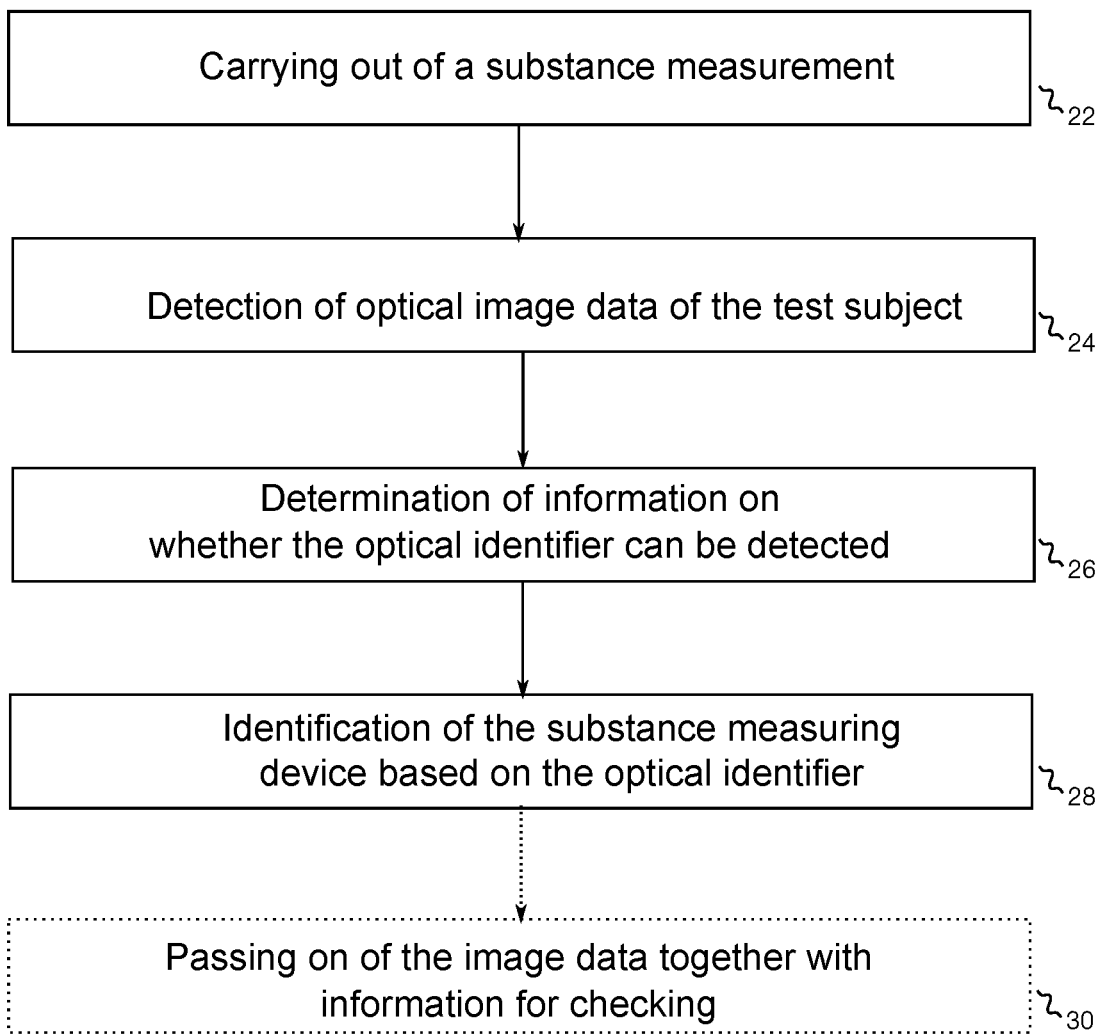
FIG. 4 is a block diagram of an exemplary embodiment of a flow chart of a process for the identification of a substance measuring device.

FIG. 4 shows a block diagram of an exemplary embodiment of a flow chart of a process for the unique and individual identification of a substance measuring device 100 of a test subject 300, cf. FIG. 2 as well. The substance measuring device 100 has an optical identifier 12. The process comprises the carrying out 22 of a substance measurement by the test subject 300. Detection 24 of optical image data of the test subject 300 together with the substance measuring device 100 during the substance measurement is then carried out. The process further comprises the determination 26 of information on whether the optical identifier 12 can be detected in the image data. Identification 28 of the substance measuring device 100 takes place based on the optical identifier 12. As FIG. 4 further shows, the passing on of the image data together with the information can also optionally be carried out for checking.

The image data recorded with the camera 200 can then be processed and the detection of the optical identifier 12 can be carried out. The camera 200 can accordingly be configured to carry out at least one of the processes described above. The camera 200 can further be integrated into a cell phone. In a further exemplary embodiment, the camera further comprises a memory (e.g., a digital memory which may be volatile or nonvolatile) and is configured to store the image data together with the information. The device 10, the camera 200 or the cell phone may correspond to a hardware component or comprise a programmable hardware component, e.g., a processor, microcontroller, etc., which is configured to execute correspondingly adapted software. Hence, a further exemplary embodiment is a program or computer program with a program code for executing one of the processes being described here, when the program code is executed on a computer, on a processor or on a programmable hardware component.

In some exemplary embodiments, information on whether or not the substance measuring device 100 (e.g., breath alcohol device) or the optical identifier 12 is present can accordingly be inserted (identification) into the image data or into the photos by software. Random samples can be selected more efficiently due to this identification. Violations, in which other persons provide the breath alcohol test for the person supposed to provide the sample, can be identified in a simple manner. In addition, manipulation with a recently purchased device or replica, in which case the correct person with the "new device" or the replica is then imaged onto the image without or with incorrect identifier, but the blowing is done into a different device, can be made difficult or even prevented.

A combination, which is as a whole also called "alcotester," of a smartphone (cell phone) and an alcohol measuring device 100 is used in an exemplary embodiment. The smartphone has a camera 200. Three highly reflective foil sections (markers) are arranged in the upper area on the rear side of the breath alcohol measuring device 100, cf. FIGS. 1, 2. In this exemplary embodiment, they are arranged together in a triangle with a minimal distance of 2 cm to one another. The flash of the smartphone camera 200 is triggered during the providing of the sample. Due to the bright light, the markers are illuminated, which are thereby, in turn, detected due to the high reflection from the camera 200 of the smartphone. Using the app of the smartphone, it is analyzed whether the defined markers were visible during the breath alcohol test. It can consequently be proven that the actual person providing the sample 300 is also the person in the photo, and that the device receiving the sample is also in the photo at the time of providing the sample. Should this not be the case, the result of the breath alcohol test will be provided with a prominent remark. This can be viewed in a prioritized manner in case of the random samples. Thus, violations can be identified in a simplified and markedly more efficient manner, cf. also FIG. 2. In addition, in some exemplary embodiments it can be checked whether the person in the photo is also the desired person, for example, by means of a face recognition/person identification software. In some exemplary embodiments, it is possible, as a result, to prevent or detect that a breath sample was given into the correct device, but it was provided by the wrong person.

In addition, it is possible to prevent a manipulation with a new device by the foil sections being provided with an individual pattern, which cannot be copied, for example, with holograms, watermarks, etc. The breath alcohol tester thus becomes unique, cf. FIG. 3. The pattern is stored in the app as a reference in the case of placement in a home monitoring program. The individual pattern (optical identifier 12) can be recognized in the form of an image comparison by means of the app and the camera 200 of the smartphone during the providing of a sample. Should a new device be purchased, the patterns would not agree and a violation would be reported.

Light sources may also be used instead of reflective foil sections. In such an exemplary embodiment, the optical identifier 12 is a sequence of optical signals, which can be generated by one or more light sources arranged on the substance measuring device 100. The light sources here may also correspond to a display, i.e., to a kind of display screen/display for displaying graphics. The light sources are configured in some exemplary embodiments to emit light in an invisible range, e.g., to emit light in an infrared (IR) range. This can offer advantages because, e.g., a black housing can be used, through which it is always possible to shine light in the IR range and which is accordingly still transparent or partly transparent in the IR range. For example, IR-LEDs (light-emitting diodes) or even a single LED (e.g., for emission in the visible range) can be installed on the rear side of the breath alcohol measuring device 100. An individual blinking pattern can rule out further manipulations in both cases.

For example, a communication connection can be established between the cell phone and the substance measuring device 100. Any desired wireless or even wired interfaces may be provided for this. Some examples are wired communication via Universal Serial Bus (USB) as well as wireless communication via Bluetooth, Near Field Communication (NFC) or Wireless Local Area Network (WLAN).

Via such a communication connection, the app of the smartphone can then actuate one or more light sources of the substance measuring device 100 and at the same time optically detect the response of the light sources via the camera 200. A sequence or even a displayed code (for example, a barcode or QR code displayed on a display) can thus also be provided with a random component as well as a device-specific identifier of the substance measuring device 100, so that different codes can also be used under the control of the app. This can further increase the certainty or the detection of attempts to deceive.

The unique and individual identification then takes place by the detection of the sequence, which can also be the result of a combination of sequences. For example, a first sequence, which is associated with the substance measuring device 100, can be combined with a second sequence, which is associated with the smartphone or with the camera 200. In some exemplary embodiments, in addition or as an alternative, a combination may also take place with a random sequence, which is newly determined individually at the time of each identification. Thus, the unique and individual identifiability is provided at least temporarily and the verification of the association or link is thus made possible. In the case of binary sequences, a transmission of a first sequence from the cell phone 200 to the substance measuring device 100, a link of the received sequence with a sequence associated with the substance measuring device 100 (e.g., an XOR (exclusive or) operation) and then with an actuation of the light sources with the resulting sequence is conceivable. The resulting sequence can then be detected and verified via the camera in the cell phone 200. The identity of the substance measuring device and thus the association with the test subject 300 can be verified on the basis of the resulting sequence. Making the reproducibility of the optical identifier difficult can be achieved by additional combination with a random sequence.

Exemplary embodiments are further based on the finding that such an identification process can be dependent on a function of the camera 200 or of the cell phone. In addition, a cell phone can have a special configuration for this purpose and possibly be correspondingly limited in its other functions as well. Such limitations may lead to a reduced suitability for daily use of such a cell phone, which limits interest in other use. A further exemplary embodiment is a cell phone, which is configured in its function for the identification of the substance measuring device 100 with the camera 200 and is limited in its other functions. For example, the cell phone may be configured to be able to make calls to no more than three, five or ten predefined telephone numbers. Such calls may comprise, for example, an emergency number, a probation officer and a freely selectable telephone number or a service number of the operator.

The features disclosed in the above description, in the claims and in the drawings may be significant for the embodiment of exemplary embodiments in the different configurations thereof both individually and in any combination and, unless something different appears from the description, they may be combined with one another as desired.

Even though some aspects were described in connection with a device, it is obvious that these aspects also represent a description of the corresponding process, so that a block or a component of a device shall also be considered to represent a corresponding process step or a feature of a process step. Analogously to this, aspects that were described in connection with a process step or as a process step also represent a description of a corresponding block or detail or feature of a corresponding device.

Depending on certain implementation requirements, exemplary embodiments of the present invention may be implemented in hardware or in software. The implementation may be carried out with the use of a digital storage medium, for example, a floppy disk, a DVD, a Blu-Ray Disc, a CD, a ROM, a PROM, an EPROM, an EEPROM or a FLASH memory, a hard drive or another magnetic or optical memory, on which electronically readable control signals are stored, which can or do interact with a programmable hardware component such that the process in question is executed.

A programmable hardware component may be formed by a processor, a computer processor (CPU=Central Processing Unit), a graphics processor (GPU=Graphics Processing Unit), a computer, a computer system, an application-specific integrated circuit (ASIC), an integrated circuit (IC), a System on Chip (SOC), a programmable logic element or a field-programmable gate array (FPGA) with a microprocessor.

The digital storage medium may therefore be machine- or computer-readable. Some exemplary embodiments consequently comprise a data storage medium, which has electronically readable control signals, which are capable of interacting with a programmable computer system or with a programmable hardware component such that one of the processes described here is executed. Thus, an exemplary embodiment is a data storage medium (or a digital storage medium or a computer-readable medium), on which the program for executing one of the processes described here is recorded.

Exemplary embodiments of the present invention may generally be implemented as program, firmware, computer program or computer program product with a program code or as data, wherein the program code or the data act such as to execute one of the processes when the program is running on a processor or on a programmable hardware component. The program code or the data may also be stored, for example, on a machine-readable medium or storage medium. The program code or the data may be present, among other things, as source code, machine code or byte code as well as as another intermediate code.

Another exemplary embodiment is, furthermore, a data stream, a signal sequence or a sequence of signals, which data stream or signal sequence represents the program for executing one of the processes being described here. The data stream, the signal sequence or the sequence of signals may be configured, for example, such as to be transferred via a data communication connection, for example, via the Internet or another network. Exemplary embodiments are thus also signal sequences representing data, which signal sequences are suitable for transmission via a network or a data communication connection, wherein the data represent the program.

A program according to an exemplary embodiment may implement one of the processes while it is executed, for example, by reading storage locations or writing a datum or a plurality of data into these, as a result of which switching operations or other processes are possibly elicited in transistor structures, in amplifier structures or in other electrical, optical, magnetic components or in components operating according to another principle of function. By reading a storage location, data, values, sensor values or other information can correspondingly be detected, determined or measured. A program can therefore detect, determine or measure variables, values, measured variables and other information by reading from one or more storage locations and bring about, trigger or execute an action as well as actuate other devices, machines and components by writing to one or more storage locations.

The above-described exemplary embodiments represent only an illustration of the principles of the present invention. It is obvious that modifications and variations of the arrangements and details described here may be obvious to other persons skilled in the art. The present invention is therefore intended to be limited only by the scope of protection of the following patent claims rather than by the specific details that were presented here on the basis of the description and the explanation of the exemplary embodiments.

While specific embodiments of the invention have been shown and described in detail to illustrate the application of the principles of the invention, it will be understood that the invention may be embodied otherwise without departing from such principles.

The invention claimed is:

1. A device for the unique and individual identification of a substance measuring device of a test subject, the device comprising an optical identifier configured for a recognition of the substance measuring device and for a verification of an association between the substance measuring device and the test subject, wherein the optical identifier comprises a geometric configuration of one or more markers, or a barcode, or a quick response (QR) code or a geometric configuration of any combination of one or more markers, a barcode, a quick response (QR) code, for a housing of the substance measuring device, wherein the geometric configuration corresponds to a configuration within a triangle, wherein the optical identifier provides an identification of the substance measuring device for determining an association between the substance measuring device and the test subject.

2. A device in accordance with claim 1, wherein the geometric configuration comprises a first geometric configuration portion, a second geometric configuration portion and a third geometric configuration portion, the first geometric configuration portion, the second geometric configuration portion and the third geometric configuration portion defining the triangle, the first geometric configuration portion, the second geometric configuration portion and the third geometric configuration portion being located at a spaced location from each other, the first geometric configuration portion being defined by a first marker, the second geometric configuration portion being defined by a second marker and the third geometric configuration portion being defined by a third marker, the first marker being arranged along a first side of the triangle, the second marker being arranged along a second side of the triangle, the third marker being arranged along a third side of the triangle.

3. A device in accordance with claim 1, wherein the optical identifier comprises one or more reflectors.

4. A device in accordance with claim 1, wherein the optical identifier comprises one or more reflective foil sections.

5. A device in accordance with claim 1, wherein the optical identifier comprises a unique identifier.

6. A device in accordance with claim 1, wherein the optical identifier comprises a sequence of optical signals, which can be generated by one or more light sources arranged at the substance measuring device.

7. A device in accordance with claim 6, wherein the light sources are configured to emit light in an invisible range.

8. A substance measuring device comprising:
a substance measuring device body; and
an identification device connected to the substance measuring device body for the unique and individual identification of the substance measuring device, the identification device comprising an optical identifier configured for a recognition of the substance measuring device and for a verification of an association between the substance measuring device and the test subject, wherein the optical identifier comprises a geometric configuration of one or more markers, or a barcode, or a quick response (QR) code or a geometric configuration of any combination of one or more markers, a barcode, a quick response (QR) code, for a housing of the substance measuring device, wherein the geometric configuration corresponds to a configuration within a triangle, the optical identifier providing an identification of the substance measuring device for determining an association between the substance measuring device and the test subject.

9. A substance measuring device in accordance with claim 8, wherein the geometric configuration comprises a first geometric configuration portion, a second geometric configuration portion and a third geometric configuration portion, the first geometric configuration portion, the second geometric configuration portion and the third geometric configuration portion defining the triangle, the first geometric configuration portion, the second geometric configuration portion and the third geometric configuration portion being located at a spaced location from each other, the first geometric configuration portion being defined by a first marker, the second geometric configuration portion being defined by a second marker and the third geometric configuration portion being defined by a third marker, the first marker being arranged along a first side of the triangle, the second marker being arranged along a second side of the triangle, the third marker being arranged along a third side of the triangle.

10. A process for the unique and individual identification of a substance measuring device of a test subject, wherein the substance measuring device has an optical identifier, the process comprising the steps of:
carrying out a substance measurement by the test subject;
detecting optical image data of the test subject together with the substance measuring device during the substance measurement;
determining information on whether the optical identifier can be detected in the image data;

identifying and recognizing the substance measuring device based on the optical identifier, wherein the optical identifier comprises a geometric configuration of one or more markers, or a barcode, or a quick response (QR) code or a geometric configuration of any combination of one or more markers, a barcode, a quick response (QR) code, for a housing of the substance measuring device, wherein the geometric configuration corresponds to a configuration within a triangle; and verifying an association between the substance measuring device and the test subject based on the optical identifier.

11. A process in accordance with claim 10, further comprising passing on of the image data together with the information for checking.

12. A process according to claim 10, further comprising:
providing a program comprising a program code for executing the steps of the processes; and
executing the program code on a computer, on a processor or on a programmable hardware component.

13. A process in accordance with claim 10, wherein the geometric configuration comprises a first geometric configuration portion, a second geometric configuration portion and a third geometric configuration portion, the first geometric configuration portion, the second geometric configuration portion and the third geometric configuration portion defining the triangle, the first geometric configuration portion, the second geometric configuration portion and the third geometric configuration portion being located at a spaced location from each other, the first geometric configuration portion being defined by a first marker, the second geometric configuration portion being defined by a second marker and the third geometric configuration portion being defined by a third marker, the first marker being arranged along a first side of the triangle, the second marker being arranged along a second side of the triangle, the third marker being arranged along a third side of the triangle.

* * * * *